US008975470B2

(12) United States Patent
Sela et al.

(10) Patent No.: US 8,975,470 B2
(45) Date of Patent: Mar. 10, 2015

(54) INTRODUCING DNA INTO PLANT CELLS

(75) Inventors: Ilan Sela, Ramot-HaShavim (IL); Haim David Rabinowitch, Kiryat-Ono (IL); Ofer Gover, Ramat-HaSharon (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 90 days.

(21) Appl. No.: 13/381,103

(22) PCT Filed: Jun. 30, 2010

(86) PCT No.: PCT/IL2010/000526
§ 371 (c)(1),
(2), (4) Date: Feb. 23, 2012

(87) PCT Pub. No.: WO2011/001434
PCT Pub. Date: Jan. 6, 2011

(65) Prior Publication Data
US 2012/0185967 A1 Jul. 19, 2012

Related U.S. Application Data

(60) Provisional application No. 61/287,435, filed on Dec. 17, 2009, provisional application No. 61/221,626, filed on Jun. 30, 2009.

(51) Int. Cl.
*A01H 5/08* (2006.01)
*C12N 15/86* (2006.01)
*C12N 15/82* (2006.01)

(52) U.S. Cl.
CPC ........ *C12N 15/8203* (2013.01); *C12N 15/8257* (2013.01); *C12N 15/8261* (2013.01)
USPC ........... 800/278; 800/280; 800/285; 800/286; 800/279; 800/317; 800/320; 435/91.42; 435/91.4; 435/320.1

(58) Field of Classification Search
None
See application file for complete search history.

(56) References Cited

U.S. PATENT DOCUMENTS

| 4,855,237 | A | | 8/1989 | Morinaga et al. | |
|---|---|---|---|---|---|
| 5,846,795 | A | * | 12/1998 | Ahlquist et al. | 435/468 |
| 6,392,121 | B1 | * | 5/2002 | Mason et al. | 800/287 |
| 2002/0083491 | A1 | * | 6/2002 | Peele et al. | 800/285 |

FOREIGN PATENT DOCUMENTS

| CN | 1425772 A * | 6/2003 |
|---|---|---|
| EP | 1348325 | 10/2003 |
| WO | WO 01/94604 | 12/2001 |
| WO | WO 2007/141790 | 12/2007 |
| WO | WO 2008/153388 | 12/2008 |
| WO | WO 2011/001434 | 1/2011 |

OTHER PUBLICATIONS

Paz et al. (Plant Cell Rep (2006) 25: pp. 206-213).*
Escaler et al. (Virology, 267, pp. 318-325 (2000).*
International Search Report and the Written Opinion Dated Oct. 15, 2010 From the International Searching Authority Re. Application No. PCT/IL2010/000526.
Kjemtrup et al. "Gene Silencing From Plant DNA Carried by a Geminivirus", The Plant Journal, XP002108259, 14(1): 91-100, Apr. 1, 1998. Abstract, Experimental Procedures.
Padidam et al. "The Role of AV2 ('Precoat') and Coat Protein in Viral Replication and Movement in Tomato Leaf Curl Geminivirus", Virology, XP002177585, 224(2): 390-404, Jan. 1, 1996. p. 393, col. 1, Lines 10-15.
Peele et al. "Silencing of a Meristemic Gene Using Geminivirus-Derived Vectors", The Plant Journal, XP001062892, 27(4): 357-366, Aug. 1, 2001. Abstract, p. 365, col. 1, Lines 23-35.
Peretz et al. "A Universal Expression/Silencing Vector in Plants [C][OA]", Plant Physiology, XP002550013, 145(4): 1251-1263, Dec. 2007. Abstract.
Saunders et al. "Complementation of African Cassava Mosaic Virus AC2 Gene Function in a Mixed Bipartite Geminivirus Infection", Journal of General Virology, 76(9): 2287-2292, Jan. 1, 1995. Abstract.
Tamilselvi et al. "A Geminivirus AYVV-Derived Shuttle Vector for Tobacco BY2 Cells", Plant Cell Reports, XP002550015, 23(1-2): 81-90, Aug. 1, 2004. Abstract, p. 83, col. 1, Lines 1-9.
Taylor et al. "Seed Enhancement", Seed Science Research, XP009139442, 8(2): 245-256, Jun. 1, 1998.
Yang et al. "Use of Tomato Yellow Leaf Curl Virus (TYLCV) Rep Gene Sequences to Engineer TYLCV Resistance in Tomato", Phytopathology, XP002321062, 94(5): 490-496, May 1, 2004. Abstract, Materials and Methods.
International Preliminary Report on Patentability Dated Jan. 12, 2012 From the International Bureau of WIPO Re. Application No. PCT/IL2010/000526.
Translation of Notification of Office Action Dated Dec. 18, 2012 From the State Intellectual Property Office of the People's Republic of China Re. Application No. 201080038459.0.
Translation of Search Report Dated Dec. 18, 2012 From the State Intellectual Property Office of the People's Republic of China Re. Application No. 201080038459.0.
Summary of Office Action Dated Mar. 14, 2012 From the National Office of Intellectual Property of Vietnam (NOIP) Re. Application No. 1-2012-00144.
Communication Pursuant to Article 94(3) EPC Dated Mar. 8, 2013 From the European Patent Office Re. Application No. 10744736.9.
Search Report and the Written Opinion Dated Mar. 6, 2013 From the Intellectual Property Office of Singapore Issued by the Austrian Patent Office on Jan. 21, 2013 Re. Application No. 201109709-4.
Translation of Notification of Office Action Dated Sep. 18, 2013 From the State Intellectual Property Office of the People's Republic of China Re. Application No. 201080038459.0.
Office Action Dated Oct. 9, 2013 From the Israel Patent Office Re. Application No. 217286 and Its Translation Into English.

(Continued)

*Primary Examiner* — David T Fox
*Assistant Examiner* — Jared Shapiro

(57) ABSTRACT

The present invention provides means and methods for simple and efficient introduction of foreign genetic material into the plant cell. Particularly, the present invention combines seed priming and virus-based DNA constructs for efficient introduction of heterologous DNA into plants.

16 Claims, 4 Drawing Sheets
(3 of 4 Drawing Sheet(s) Filed in Color)

(56) References Cited

OTHER PUBLICATIONS

Communication Pursuant to Article 94(3) EPC Dated Jan. 8, 2014 From the European Patent Office Re. Application No. 10744736.9.
Patent Examination Report Dated Nov. 19, 2013 From the Australian Government, IP Australia Re. Application No. 2010267537.
Second Written Opinion Dated Jan. 24, 2014 From the Intellectual Property Office of Singapore Issued by the Austrian Patent Office Re. Application No. 201109709-4.
Notification of Office Action Dated Apr. 4, 2014 From the State Intellectual Property Office of the People's Republic of China Re. Application No. 201080038459.0.
Communication Pursuant to Rule 114(2) EPC Dated Feb. 14, 2014 From the European Patent Office Re. Application No. 10744736.9.
Communication Pursuant to Article 94(3) EPC Dated Sep. 4, 2014 From the European Patent Office Re. Application No. 10744736.9.
Request for Examination Dated Jun. 23, 2014 From the Rospatent, Federal Service for Intellectual Property, Federal State Budgetary Institution, Federal Institute of industrial Property of the Russian Federation Re. Application No. 2012103038 and Its Translation Into English.
Domaradskiy "Osnovy Virusoligii Dlya Ekologov [Introduction to Virology for Ecologists]", Lex Est., p. 43, 2007. & English Abstract of p. 43.
Filimonov et al. "The Permeability of the Cells and Tissues. Laboratory Operations Manual on Course 'Biophysics' for Biological Faculty Students of Specialities G31.01.01 'Biology', H33.01.01 'Bioecology'", Belarusian State University, Faculty of Biology, Department of Biochemistry, Minsk, p. 4-8, 10-11, 2003. & English Machine Translation.
Examination Report Dated Oct. 14, 2014 From the Intellectual Property Office of Singapore Re. Application No. 201109709-4.
Notice of Reason for Rejection Dated Sep. 12, 2014 From the Japanese Patent Office Re. Application No. 2012-519117 and Its Translation Into English.

* cited by examiner

SEQUENCE LISTING

<160> NUMBER OF SEQ ID NOS: 8

<210> SEQ ID NO 1
<211> LENGTH: 2722
<212> TYPE: DNA
<213> ORGANISM: Artificial Sequence
<220> FEATURE:
<223> OTHER INFORMATION: IL-60

<400> SEQUENCE: 1

```
gttgaaatga atcggtgtct ctcaaagctc tatggcaatc ggtgtatcgg tgtcttactt      60
atacctggac acctaatggc tatttggtaa tttcataaat gttcattgca attcaaaatt     120
caaaattcaa aaatcaaatc tttaaagcgg ccatccgtat aatattaccg gatggccgcg     180 cctttttgttt ttatgtggtc cccacgaggg ttacacagac gtcactgtca accaatcaaa    240
ttgcattctc aaacgttaga taagtgttca tttgtcttta tatacttggt ccccaagttt     300
tttgtcttgc aatatgtggg acccacttct taatgaattt cctgaatctg ttcacggatt     360
tcgttgtatg ttagctatta aatatttgca gtccgttgag gaaacttacg agcccaatac     420
attgggccac gatttaatta gggatcttat atctgttgta agggccccgt gactatgtcg     480
aagcgaccag gcgatataat catttccacg cccgtctcga aggttcgccg aaggctgaac    540
ttcgacggcc catacaggcc catgtaccga aagcccagaa atacagaatg tatcgaagcc    600
ctgatgttcc ccgtggatgt gaaggcccct ttaaagtcca gtcttatgag caacgggatg   660
atattaagca tcctggtatt gttcggttgt gttagtgatg ttactcgtgg atctggaatt    720
actcacagag tgggtaagag gttctgtgtt aaatcgatat attttttagg taaagtctgg    780
atggatgaaa atatcaagaa gcagaatcac actaatcagg tcatgttctt cttggtccgt    840
gatagaaggc cctatggaaa cagcccaatg gattttggac aggttttttaa tatgttcgat   900 aatgagccca gtaccgcaac cgtgaagaat gatttgcgtg ataggtttca agtgatgagg  960
aaatttcatg ctacagttat tggtgggccc tctggaatga aggaacaggc attagttaag  1020
agatttttta aaattaacag tcatgtaact tataatcatc aggaggcagc aaagtacgag  1080
aaccatactg aaaacgcctt gttattgtat atggcatgta cgcatgcctc taatccagtg  1140
```

-continued

| | |
|---|---|
| tatgcaacta tgaaaatacg catctatttc tatgattcaa tatcaaatta ataaaattta | 1200 |
| tattttatat catgagtttc tgttacattt attgtgtttt caagtacatc atacaataca | 1260 |
| tgatcaactg ctctgattac attgttaatg gaaattacac caagactatc taaatactta | 1320 |
| agaacttcat atctaaatac tcttaagaaa tgaccagtct gaggctgtaa tgtcgtccaa | 1380 |
| attcggaagt tgagaaaaca tttgtgaatc cccattacct tcctgatgtt gtggttgaat | 1440 |
| cttatctgaa tggaaatgat gtcgtggttc attagaaatg gcctctggct gtgttctgtt | 1500 |
| atcttgaaat agagggggat tgttatctcc cagataaaaa cgccattctc tgcctgagga | 1560 |
| gcagtgatga gttcccctgt gcgtgaatcc atgattattg cagttgaggt ggaggtagta | 1620 |
| tgagcagcca cagtctaggt ctacacgctt acgccttatt ggtttcttct tggctatctt | 1680 |
| gtgttggacc ttgattgata cttgcgaaca gtggctcgta gagggtgacg aaggttgcat | 1740 |
| tcttgagagc ccaattttc aaggatatgt ttttttcttc gtctagatat tccctatatg | 1800 |
| atgaggtagg tcctggattg cagaggaaga tagtgggaat tcccccttta atttgaatgg | 1860 |
| gcttcccgta ctttgtgttg ctttgccagt ccctctgggc cccatgaat tccttgaagt | 1920 |
| gctttaaata atgcgggtct acgtcatcaa tgacgttgta ccacgcatca ttactgtaca | 1980 |
| cctttgggct taggtctaga tgtccacata ataattatg tgggcctaga gacctggccc | 2040 |
| acattgtttt gcctgttctg ctatcaccct caatgacaat acttatgggt ctccatggcc | 2100 |
| gcgcagcgga atacacgacg ttctcggcga cccactcttc aagttcatct ggaacttgat | 2160 |
| taaagaaga agaaagaaat ggagaaacat aaacttctaa aggaggacta aaaatcctat | 2220 |
| ctaaatttga acttaaatta tgaaattgta aaatatagtc ctttggggcc ttctctttta | 2280 |
| atatattgag ggcctcggat ttactgcctg aattgagtgc ttcggcatat cgtcgttgg | 2340 |
| cagattgctg acctcctcta gctgatctgc catcgatttg gaaaactcca aaatcaatga | 2400 |
| agtctccgtc tttctccacg taggtcttga catctgttga gctcttagct gcctgaatgt | 2460 |
| tcggatggaa atgtgctgac ctgtttggtg ataccaggtc gaagaaccgt tggttcttac | 2520 |
| attggtatt gccttcgaat tggataagca catggagatg tggttcccca ttctcgtgga | 2580 |
| gttctctgca aactttgatg tattttttat ttgttgggt ttctaggttt tttaattggg | 2640 |
| aaagtgcttc ctctttagag agagaacaat tgggatatgt taggaaataa tttttggcat | 2700 |
| atattttaaa taaacgaggc at | 2722 |

<210> SEQ ID NO 2
<211> LENGTH: 5509
<212> TYPE: DNA
<213> ORGANISM: Artificial Sequence
<220> FEATURE:
<223> OTHER INFORMATION: IL-60-BS

<400> SEQUENCE: 2

| | |
|---|---|
| gttgaaatga atcggtgtct ctcaaagctc tatggcaatc ggtgtatcgg tgtcttactt | 60 |
| atacctggac acctaatggc tatttggtaa tttcataaat gttcattgca attcaaaatt | 120 |
| caaaattcaa aaatcaaatc tttaaagcgg ccatccgtat aatattaccg gatggccgcg | 180 |
| ccttttgttt ttatgtggtc cccacgaggg ttacacagac gtcactgtca accaatcaaa | 240 |
| ttgcattctc aaacgttaga taagtgttca tttgtcttta tatacttggt ccccaagttt | 300 |
| tttgtcttgc aatatgtggg acccacttct taatgaattt cctgaatctg ttcacggatt | 360 |
| tcgttgtatg ttagctatta aatatttgca gtccgttgag gaaacttacg agcccaatac | 420 |
| attgggccac gatttaatta gggatcttat atctgttgta agggccccgt gactatgtcg | 480 |

```
aagcgaccag gcgatataat catttccacg cccgtctcga aggttcgccg aaggctgaac    540
ttcgacggcc catacaggcc catgtaccga aagcccagaa atacagaatg tatcgaagcc    600
ctgatgttcc ccgtggatgt gaaggcccct ttaaagtcca gtcttatgag caacgggatg    660
atattaagca tcctggtatt gttcggttgt gttagtgatg ttactcgtgg atctggaatt    720
actcacagag tgggtaagag gttctgtgtt aaatcgatat attttttagg taaagtctgg    780
atggatgaaa atatcaagaa gcagaatcac actaatcagg tcatgttctt cttggtccgt    840
gatagaaggc cctatggaaa cagcccaatg gattttggac aggttttta tatgttcgat     900 aatgagccca gtaccgcaac cgtgaagaat gatttgcgtg ataggtttca agtgatgagg    960
aaatttcatg ctacagttat tggtgggccc tctggaatga aggaacaggc attagttaag   1020 agattttta aaattaacag tcatgtaact tataatcatc aggaggcagc aaagtacgag    1080
aaccatactg aaaacgcctt gttattgtat atggcatgta cgcatgcctc taatccagtg   1140
tatgcaacta tgaaaatacg catctatttc tatgattcaa tatcaaatta ataaaattta   1200
tattttatat catgagtttc tgttacattt attgtgtttt caagtacatc atacaataca   1260
tgatcaactg ctctgattac attgttaatg gaaattacac caagactatc taaatactta   1320
agaacttcat atctaaatac tcttaagaaa tgaccagtct gaggctgtaa tgtcgtccaa   1380
attcggaagt tgagaaaaca tttgtgaatc cccattacct tcctgatgtt gtggttgaat   1440
cttatctgaa tggaaatgat gtcgtggttc attagaaatg gcctctggct gtgttctgtt   1500
atcttgaaat agaggggggat tgttatctcc cagataaaaa cgccattctc tgcctgagga   1560
gcagtgatga gttcccctgt gcgtgaatcc atgattattg cagttgaggt ggaggtagta   1620
tgagcagcca cagtctaggt ctacacgctt acgccttatt ggtttcttct tggctatctt   1680
gtgttggacc ttgattgata cttgcgaaca gtggctcgta gagggtgacg aaggttgcat   1740
tcttgagagc ccaattttc aaggatatgt ttttttcttc gtctagatat tccctatatg    1800
atgaggtagg tcctggattg cagaggaaga tagtgggaat tcccccttta atttgaatgg   1860
gcttcccgta ctttgtgttg ctttgccagt ccctctgggc cccatgaat tccttgaagt    1920 gctttaaata atgcgggtct acgtcatcaa tgacgttgta ccacgcatca ttactgtaca   1980
cctttgggct taggtctaga tgtccacata ataattatg tgggcctaga gacctggccc    2040
acattgtttt gcctgttctg ctatcaccct caatgacaat acttatgggt ctccatggcc   2100
gcgcagcgga atacacgacg ttctcggcga cccactcttc aagttcatct ggaacttgat   2160
taaaagaaga agaaagaaat ggagaaacat aaacttctaa aggaggacta aaaatcctat   2220
ctaaatttga acttaaatta tgaaattgta aaatatagtc ctttggggcc ttctctttta   2280
atatattgag ggcctcggat ttactgcctg aattgagtgc ttcggcatat gcgtcgttgg   2340
cagattgctg acctcctcta gctgatctgc catcgatttg gaaaactcca aaatcaatga   2400
agtctccgtc tttctccacg taggtcttga catctgttga gctcttagct gcctgaatgt   2460
tcggatggaa atgtgctgac ctgtttgggg ataccaagtc gaagaaccgt tggttcttac   2520
attggtattt gccttcgaat tggataagca catggagatg tggttcccca ttctcgtgga   2580
gttctttgca aactttgatg tatttttat ttgttggggt ttctagtttt tttaattggg    2640
aaagtgcttc ctctttagag agagaacaat tgggatatgt taggaaataa ttttggcat    2700 atattttaaa taaacgaggc atgttgaaat gaatcggtgt ccctcaaagc tctatggcaa   2760
tcggtgtatc ggtgtcttac ttatacttgg acacctaatg gctatttggt aatttcataa   2820
```

```
atgttcattt caattcaaaa ttcaaaattc aaaaatcaaa tcattaaagc ggccatccgt   2880
ataatattac cggatggccg cgccttttcc ttttatgtgg tccccacgag ggttacacag   2940
atgttattgt caaccaatca aattgcattc tcaaacgtta gataagtgtt catttgtctt   3000
tatatacttg gtccccaagt tttttgtctt gcaatatgtg ggacccactt cttaatgaat   3060
ttcctgaatc tgttcacgga tttcgttgta tgttagctat aaatatttg cagtccgttg    3120
aggaaactta cgagcccaat acattgggcc acgatttaat tagggatctt atatctgttg   3180
taagggcccg tgactatgtc gaagcgacca ggcgatataa tcatttccac gcccgtctcg   3240
aaggttcgcc gaaggctgaa cttcgacagc ccatacagca gccgtgctgc tgtccccatt   3300
gtccaaggca caaacaagcg acgatcatgg acgtacaggc ccatgtaccg aaagcccaga   3360
atatacagaa tgtatcgaag ccctgatgtt ccccgtggat gtgaaggccc atgtaaagtc   3420
cagtcttatg agcaacggga tgatattaag catactggta ttgttcgttg tgttagtgat   3480
gttactcgtg gatctggaat tactcacaga gtgggtaaga ggttctgtgt taaatcgata   3540
tatttttag gtaaagtctg gatggatgaa atatcaaga agcagaatca cactaatcag     3600
gtcatgttct tcttggtccg tgatagaagg ccctatggaa acagcccaat ggattttgga   3660
caggtttta atatgttcga taatgagccc agtaccgcaa ccgtgaagaa tgatttgcgt    3720
gataggtttc aagtgatgag gaaatttcat gctacagtta ttggtgggcc ctctggaatg   3780
aaggaacagg cattagttaa gagattttt aaaattaaca gtcatgtaac tttatttata    3840
ttcattcagg aggcagcaaa gtacgagaac catactgaaa acgccttgtt attgtatatg   3900
gcatgtacgc atgcctctaa tccagtgtat gcaactgatga aaatacgcat ctatttctat  3960
gattcaatat caaattaata aaatttatat tttatatcat gagtttctgt tacatttatt   4020
gtgttttcaa gtacatcata caatacatga tcaactgctc tgattacatt gttaatggaa   4080
attacaccaa gactatctaa atacttaaga acttcatatc taaatactct taagaaatga   4140
ccagtctgag gctgtaatgt cgtccaaatt cggaagtcga gaaaacattt gtgaatcccc   4200
attaccttcc tgatgttgtg gttgaatctt atctgaatgg aaatgatgtc gtggttcatt   4260
agaaatggcc tctggctgtg ttctgttatc ttgaaataga ggggattgtt tatctcccag   4320
ataaaaacgc cattctctgc ctgaggagca gtgatgagtt cccctgtgcg tgaatccatg   4380
attattgcag ttgaggtgga ggtagtatga gcagccacag tctaggtcta cacgcttacg   4440
ccttattggt ttcttcttgg ctatcttgtg ttggaccttg attgatactt gcgaacagtg   4500
gctcgtagag ggtgacgaag gttgcattct tgagagccca atttttcaag gatatgtttt   4560
tttcttcgtc tagatattcc ctatatgagg aggtaggtcc tggattgcag aggaagatag   4620
tgggaattcc cccctttaatt tgaatgggct tcccgtactt tgtgttgctt tgccagtccc   4680
tctgggcccc catgaattcc ttgaagtgct ttaaataatg cgggtctacg tcatcaatga   4740
cgttgtacca cgcatcatta ctgtacacct tgggcttag gtctagatgt ccacataaat    4800
aattatgtgg gcctagagac ctggcccaca ttgttttgcc tgttctgcta tcaccctcaa   4860
tgacaatact tatgggtctc catggccgcg cagcggaata cacgacgttc tcggcgaccc   4920
actcttcaag ttcatctgga acttgattaa agaagaagaa aagaaatgga gaaacataaa   4980
cttctaaagg aggactaaaa atcctatcta aatttgaact taaattatga aattgtaaaa   5040
tatagtcctt tggggccttc tcttttaata tattgagggc ctcggattta ctgcctgaat   5100
tgagtgcttc ggcatatgcg tcgttggcag attgctgacc tcctctagct gatctgccat   5160
cgatttggga aactccaaaa tcaatgaagt ttccgtcttt ctccacgtag gtcttgacat   5220
```
ctgttgagct cttagctgcc tgaatgttcg gatggaaatg tgctgacctg tttggtgata 5280
ccaggtcgaa gaaccgttgg ttcttacatt ggtatttgcc ttcgaattgg ataagcacat 5340
ggagatgtgg ttccccattc tcgtggagtt ctctgcaaac tttgatgtat tttttatttg 5400
ttggggtttc taggtttttt aattgggaaa gtgcttcctc tttagagaga gaacaattgg 5460
gatatgttag gaaataattt ttggcatata ttttaaataa acgaggcat 5509

<210> SEQ ID NO 3
<211> LENGTH: 238
<212> TYPE: PRT
<213> ORGANISM: Artificial Sequence
<220> FEATURE:
<223> OTHER INFORMATION: IL-60 coat protein
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 3

```
Met Ser Xaa Arg Pro Gly Asp Ile Ile Ile Ser Thr Pro Val Ser Lys
1               5                   10                  15

Val Arg Arg Arg Leu Asn Phe Xaa Gly Pro Tyr Arg Xaa Met Tyr Arg
            20                  25                  30

Lys Pro Arg Asn Thr Glu Cys Ile Glu Ala Leu Met Phe Pro Val Asp
        35                  40                  45

Val Lys Ala Pro Leu Lys Xaa Ser Xaa Met Ser Asn Gly Met Ile Leu
    50                  55                  60

Ser Xaa Leu Val Leu Phe Gly Cys Val Xaa Asp Val Thr Xaa Gly Ser
65                  70                  75                  80

Gly Ile Thr His Arg Val Gly Lys Arg Phe Cys Val Lys Ser Ile Tyr
                85                  90                  95

Phe Leu Gly Lys Val Trp Met Asp Glu Asn Ile Lys Lys Gln Asn His
            100                 105                 110

Thr Asn Gln Val Met Phe Phe Leu Val Arg Asp Arg Arg Pro Tyr Gly
        115                 120                 125

Asn Ser Pro Met Asp Phe Gly Gln Val Phe Asn Met Phe Asp Asn Glu
    130                 135                 140
```

-continued

```
Pro Ser Thr Ala Thr Val Lys Asn Asp Leu Arg Asp Arg Phe Gln Val
145                 150                 155                 160

Met Arg Lys Phe His Ala Thr Val Ile Gly Gly Pro Ser Gly Met Lys
                165                 170                 175

Glu Gln Ala Leu Val Lys Arg Phe Phe Lys Ile Asn Ser His Val Thr
            180                 185                 190

Tyr Asn His Gln Glu Ala Ala Lys Tyr Glu Asn His Thr Glu Asn Ala
        195                 200                 205

Leu Leu Leu Tyr Met Ala Cys Thr His Ala Ser Asn Pro Val Tyr Ala
    210                 215                 220

Thr Met Lys Ile Arg Ile Tyr Phe Tyr Asp Ser Ile Ser Asn
225                 230                 235

<210> SEQ ID NO 4
<211> LENGTH: 116
<212> TYPE: PRT
<213> ORGANISM: tomato yellow leaf curl virus

<400> SEQUENCE: 4

Met Trp Asp Pro Leu Leu Asn Glu Phe Pro Glu Ser Val His Gly Phe
1               5                   10                  15

Arg Cys Met Leu Ala Ile Lys Tyr Leu Gln Ser Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Lys Ala Gln Asn Ile Gln Asn
            100                 105                 110

Val Ser Lys Pro
        115

<210> SEQ ID NO 5
<211> LENGTH: 98
<212> TYPE: PRT
<213> ORGANISM: tomato yellow leaf curl virus

<400> SEQUENCE: 5

Arg Met Gly Asn His Ile Ser Met Cys Leu Ser Asn Ser Lys Ala Asn
1               5                   10                  15

Thr Asn Val Arg Thr Asn Gly Ser Ser Thr Trp Tyr Pro Gln Thr Gly
            20                  25                  30

Gln His Ile Ser Ile Arg Thr Phe Arg Gln Leu Arg Ala Gln Gln Met
        35                  40                  45

Ser Arg Pro Thr Trp Arg Lys Thr Glu Thr Ser Leu Ile Leu Glu Phe
    50                  55                  60

Pro Lys Ser Met Ala Asp Gln Leu Glu Glu Val Ser Asn Leu Pro Thr
65                  70                  75                  80

Thr His Met Pro Lys His Ser Ile Gln Ala Val Asn Pro Arg Pro Ser
                85                  90                  95

Ile Tyr
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
attgatcagc gttggtggga                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
tgcggtcgcg agtgaagatc                                              20

<210> SEQ ID NO 8
<211> LENGTH: 6035
<212> TYPE: DNA
<213> ORGANISM: Artificial Sequence
<220> FEATURE:
<223> OTHER INFORMATION: pIR-GUS
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t

<400> SEQUENCE: 8
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagctcta     240
atacgactca ctatagggaa agctcggtac cacgcatgct gcagacgcgt tacgtatcgg     300
atccagaatt cgtgatatct gaattcatac ctggacacct aatggctatt tggtaatttc     360
ataaatgttc attgcaattc aaaattcaaa attcaaaaat caaatcttta aagcggccat     420
ccgtataata ttaccggatg gccgcgcctt ttgtttttat gtggtcccca cgagggttac     480
acagacgtca ctgtcaacca atcaaattgc attctcaaac gttagataag tgttcatttg     540
tctttatata cttggtcccc aagttttttg tcttgcaata tgtgggaccc acttcttaat     600
gaatttcctg aatctgttca cggatttcgt tgtatgttag ctattaaata tttgcagtcc     660
gttgaggaaa cttacgagcc caatacattg ggccacgatt taattangga tcttatatct     720
gttgtaaggg cccngtgacg aattcgtcga catgttacgt cctgtagaaa ccccaacccg     780
tgaaatcaaa aaactcgacg gcctgtgggc attcagtctg gatcgcgaaa actgtggaat     840
tgatcagcgt tggtgggaaa gcgcgttaca agaaagccgg gcaattgctg tgccaggcag     900
ttttaacgat cagttcgccg atgcagatat tcgtaattat gcgggcaacg tctggtatca     960
gcgcgaagtc tttataccga aaggttgggc aggccagcgt atcgtgctgc gtttcgatgc    1020
ggtcactcat tacggcaaag tgtgggtcaa taatcaggaa gtgatggagc atcagggcgg    1080
ctatacgcca tttgaagccg atgtcacgcc gtatgttatt gccggaaaaa gtgtacgtat    1140
```

```
caccgtttgt gtgaacaacg aactgaactg gcagactatc ccgccgggaa tggtgattac    1200
cgacgaaaac ggcaagaaaa agcagtctta cttccatgat ttctttaact atgccgggat    1260
ccatcgcagc gtaatgctct acaccacgcc gaacacctgg gtggacgata tcaccgtggt    1320
gacgcatgtc gcgcaagact gtaaccacgc gtctgttgac tggcaggtgg tggccaatgg    1380
tgatgtcagc gttgaactgc gtgatgcgga tcaacaggtg gttgcaactg acaaggcac     1440
tagcgggact ttgcaagtgg tgaatccgca cctctggcaa ccgggtgaag gttatctcta    1500
tgaactgtgc gtcacagcca aaagccagac agagtgtgat atctacccgc ttcgcgtcgg    1560
catccggtca gtggcagtga agggcgaaca gttcctgatt aaccacaaac cgttctactt    1620
tactggcttt ggtcgtcatg aagatgcgga cttacgtggc aaaggattcg ataacgtgct    1680
gatggtgcac gaccacgcat taatggactg gattggggcc aactcctacc gtacctcgca    1740
ttacccttac gctgaagaga tgctcgactg gcagatgaa catggcatcg tggtgattga     1800
tgaaactgct gctgtcggct ttaacctctc tttaggcatt ggtttcgaag cgggcaacaa    1860
gccgaaagaa ctgtacagcg aagaggcagt caacgtggaa actcagcaag cgcacttaca    1920
ggcgattaaa gagctgatag cgcgtgacaa aaaccaccca agcgtggtga tgtggagtat    1980
tgccaacgaa ccggataccc gtccgcaagt gcacgggaat atttcgccac tggcggaagc    2040
aacgcgtaaa ctcgacccga cgcgtccgat cacctgcgtc aatgtaatgt tctgcgacgc    2100
tcacaccgat accatcagcg atctctttga tgtgctgtgc ctgaaccgtt attacggatg    2160
gtatgtccaa agcggcgatt tggaaacggc agagaaggta ctggaaaaag aacttctggc    2220
ctggcaggag aaactgcatc agccgattat catcaccgaa tacggcgtgg atacgttagc    2280
cgggctgcac tcaatgtaca ccgacatgtg gagtgaagag tatcagtgtg catggctgga    2340
tatgtatcac cgcgtctttg atcgcgtcag cgccgtcgtc ggtgaacagg tatggaattt    2400
cgccgatttt gcgacctcgc aaggcatatt gcgcgttggc ggtaacaaga aagggatctt    2460
cactcgcgac cgcaaaccga gtcggcggc ttttctgctg caaaaacgct ggactggcat     2520
gaacttcggt gaaaaaccgc agcagggagg caaacagtcg acatcagctc gcggccgctg    2580
tattctatag tgtcacctaa atggccgcac aattcactgg ccgtcgtttt acaacgtcgt    2640
gactgggaaa accctggcgt tacccaactt aatcgccttg cagcacatcc ccctttcgcc    2700
agctggcgta atagcgaaga ggcccgcacc gatcgccctt cccaacagtt gcgcagcctg    2760
aatggcgaat ggaaattgta agcgttaata ttttgttaaa attcgcgtta aattttgtt    2820
aaatcagctc atttttaac caataggccg aaatcggcaa atcccttat aaatcaaaag      2880
aatagaccga gatagggttg agtgttgttc cagtttggaa caagagtcca ctattaaaga    2940
acgtggactc caacgtcaaa gggcgaaaaa ccgtctatca gggcgatggc ccactacgtg    3000
aaccatcacc ctaatcaagt tttttggggt cgaggtgccg taaagcacta atcggaacc     3060
ctaaagggag cccccgattt agagcttgac ggggaaagcc ggcgaacgtg cgagaaagg     3120
aagggaagaa agcgaaagga gcgggcgcta gggcgctggc aagtgtagcg tcacgctgc     3180
gcgtaaccac cacacccgcc gcgcttaatg cgccgctaca gggcgcgtca ggtggcactt    3240
ttcggggaaa tgtgcgcgga acccctattt gtttattttt ctaaatacat tcaaatatgt    3300
atccgctcat gagacaataa ccctgataaa tgcttcaata atattgaaaa aggaagagta    3360
tgagtattca acatttccgt gtcgccctta ttcccttttt tgcggcattt tgccttcctg    3420
ttttttgctca cccagaaacg ctggtgaaag taaaagatgc tgaagatcag ttgggtgcac   3480
```

-continued

```
gagtgggtta catcgaactg gatctcaaca gcggtaagat ccttgagagt tttcgccccg    3540
aagaacgttt tccaatgatg agcactttta aagttctgct atgtggcgcg gtattatccc    3600
gtattgacgc cgggcaagag caactcggtc gccgcataca ctattctcag aatgacttgg    3660
ttgagtactc accagtcaca gaaaagcatc ttacgcgatgg catgacagta agagaattat   3720
gcagtgctgc cataaccatg agtgataaca ctgcggccaa cttacttctg acaacgatcg    3780
gaggaccgaa ggagctaacc gcttttttgc acaacatggg ggatcatgta actgccttg    3840
atcgttggga accggagctg aatgaagcca taccaaacga cgagcgtgac accacgatgc    3900
ctgtagcaat ggcaacaacg ttgcgcaaac tattaactgg cgaactactt actctagctt    3960
cccggcaaca attaatagac tggatggagg cggataaagt tgcaggacca cttctgcgct    4020
cggcccttcc ggctggctgg tttattgctg ataaatctgg agccggtgag cgtgggtctc    4080
gcggtatcat tgcagcactg gggccagatg gtaagccctc ccgtatcgta gttatctaca    4140
cgacggggag tcaggcaact atggatgaac gaaatagaca gatcgctgag ataggtgcct    4200
cactgattaa gcattggtaa ctgtcagacc aagtttactc atatatactt tagattgatt    4260
taaaacttca ttttttaattt aaaaggatct aggtgaagat ccttttttgat aatctcatga   4320
acaataaaac tgtctgctta cataaacagt aatacaaggg gtgttatgag ccatattcaa    4380
cgggaaacgt cttgctctag gccgcgatta aattccaaca tggatgctga tttatatggg    4440
tataaatggg ctcgcgataa tgtcgggcaa tcaggtgcga caatctatcg attgtatggg    4500
aagcccgatg cgccagagtt gtttctgaaa catggcaaag gtagcgttgc caatgatgtt    4560
acagatgaga tggtcagact aaactggctg acggaattta tgcctcttcc gaccatcaag    4620
catttatcc gtactcctga tgatgcatgg ttactcacca ctgcgatccc cgggaaaaca    4680
gcattccagg tattagaaga atatcctgat tcaggtgaaa atattgttga tgcgctggca    4740
gtgttcctgc gccggttgca ttcgattcct gtttgtaatt gtccttttaa cagcgatcgc    4800
gtatttcgtc tcgctcaggc gcaatcacga atgaataacg gtttggttga tgcgagtgat    4860
tttgatgacg agcgtaatgg ctggcctgtt gaacaagtct ggaaagaaat gcataaactt    4920
ttgccattct caccggattc agtcgtcact catggtgatt tctcacttga taaccttatt    4980
tttgacgagg ggaaattaat aggttgtatt gatgttggac gagtcggaat cgcagaccga    5040
taccaggatc ttgccatcct atggaactgc ctcggtgagt tttctccttc attacagaaa    5100
cggctttttc aaaaatatgg tattgataat cctgatatga ataaattgca gtttcatttg    5160
atgctcgatg agttttttcta agaattaatt catgaccaaa atcccttaac gtgagttttc    5220
gttccactga gcgtcagacc ccgtagaaaa gatcaaagga tcttcttgag atccttttttt   5280
tctgcgcgta atctgctgct tgcaaacaaa aaaaccaccg ctaccagcgg tggtttgttt    5340
gccggatcaa gagctaccaa ctcttttttcc gaaggtaact ggcttcagca gagcgcagat    5400
accaaatact gtccttctag tgtagccgta gttaggccac cacttcaaga actctgtagc    5460
accgcctaca tacctcgctc tgctaatcct gttaccagtg gctgctgcca gtggcgataa    5520
gtcgtgtctt accgggttgg actcaagacg atagttaccg gataaggcgc agcggtcggg    5580
ctgaacgggg ggttcgtgca cacagcccag cttggagcga acgacctaca ccgaactgag    5640
atacctacag cgtgagctat gagaaagcgc cacgcttccc gaagggagaa aggcggacag    5700
gtatccggta agcggcaggg tcggaacagg agagcgcacg agggagcttc caggggaaa    5760
cgcctggtat ctttatagtc ctgtcgggtt tcgccacctc tgacttgagc gtcgattttt    5820
gtgatgctcg tcaggggggc ggagcctatg gaaaaacgcc agcaacgcgg ccttttttacg   5880
```

```
gttcctggcc ttttgctggc cttttgctca catgttcttt cctgcgttat cccctgattc    5940
tgtggataac cgtattaccg cctttgagtg agctgatacc gctcgccgca gccgaacgac    6000
cgagcgcagc gagtcagtga gcgaggaagc ggaag                                6035
```

INTRODUCING DNA INTO PLANT CELLS

RELATED APPLICATIONS

This application is a National Phase of PCT Patent Application No. PCT/IL2010/000526 having International filing date of Jun. 30, 2010, which claims the benefit of priority of U.S. Provisional Patent Application Nos. 61/287,435 filed on Dec. 17, 2009, and 61/221,626 filed on Jun. 30, 2009. The contents of the above applications are all incorporated herein by reference.

FIELD OF THE INVENTION

The present invention relates to the field of plant molecular biology, particularly to means and methods for simple and efficient introduction of exogenous genetic material into the plant cell.

BACKGROUND OF THE INVENTION

Plants carrying one or more expressible heterologous genes have a variety of potential advantages. The plants carrying a gene expression cassette may carry one or more genes which confer desired traits, including for example, herbicide, pesticide or insect tolerance; tolerance to stress; enhanced flavor and/or shelf life of the fresh produce (fruit, vegetable, seeds etc.), as well as the ability to amplify the synthesis of useful plant endogenous and/or foreign proteins, sugars, fatty-acids or secondary metabolites for consumption by man and/or animals or for use as raw materials in a variety of industries (cosmetics, pharmaceuticals, nutraceutics, foods, paper, fibers, etc.).

Current transformation technologies provide an opportunity to engineer plants with desired traits, and major advances in plant transformation have been occurred in recent years. The most common technology is mediated by *Agrobacterium tumefaciens*. Other methods of transformation are direct DNA transfer including microinjection, electroporation, particles bombardment and viral vectors (Birch R G. 1997. Annu. Rev. Plant Physiol. Plant Mol. Biol. 48:297-326). With the exception of viral vectors, application of the above techniques results in the penetration of foreign DNA into the treated cells/tissue, its integration into the treated plant's genome and the regeneration of transgenic plants. However, in many major crop plants, serious genotype limitations still exist. Transformation of some agriculturally important crop plants continues to be both difficult and time consuming. In addition, in all the aforementioned technologies, transformation is conducted with vegetative tissues (including embryos) the efficiency of transformation is poor, markers for selection are required, and the percentage of successful regeneration of a plant from the transformed cell or tissue is rather low.

Integration of the foreign DNA into the plant genome is not always desirable, particularly when genetically modified (GMO) plants arouse environmental and political issues. In these cases, methods enabling the expression of the heterologous gene(s) that are not incorporated into the host genome are required.

International (PCT) Application Publication No. WO 2007/141790 to some of the inventors of the present invention discloses modified Geminivirus-based constructs capable of spreading from one plant cell to the other within the treated plant and concomitantly introducing foreign DNA into the plant cells, without exerting the pathological virus symptoms. This foreign DNA is expressed in the plant tissues but is not integrated into its genome. The constructs (also referred to as expression vectors, IL-60 being one example) comprise the heterologous polynucleotide sequence that interrupts the Geminivirus replicase genes such that it is flanked by a non-contiguous nucleic acid sequence encoding a Geminivirus replicase or replicase-associated protein.

Seed priming is a process for treating plant seeds that enables them to undergo faster and more uniform germination on sowing or planting compared to non-treated seeds. Additionally, priming offers an optional simultaneous treatment with fungicide/pesticides/fertilizers or other chemicals (e.g. coating, pelleting, coloring as a trade mark, and more) providing protection and/or facilitating germination, emergence and seedlings establishment.

Priming allows the seeds to absorb enough water to enable their pre-germinative metabolic processes to begin and then arrests them at that stage. The amount of water absorbed (with or without beneficial chemicals) must be carefully controlled, as too much would simply allow the seed to germinate and too little would result in the seed ageing. Once the correct amount of water has been absorbed, the seeds may be sown or dried back to the original water content for storage. The primed seeds usually germinate and emerge more quickly and uniformly and the seedling vigor is typically higher compared to unprimed seeds, particularly under suboptimal conditions. The benefits gained by priming, such as rate and uniformity of germination are usually attributed to the initiation of DNA-repair processes, protein hydration enzyme activation and additional processes occurring in the early stages of germination.

The three major techniques used for controlled water uptake include priming with aqueous solutions, with hydrated solid particulate systems or by controlled hydration with water. Priming with solution is based on immersing the seeds in osmotic solution, typically PEG solutions characterized by osmotic potential that enables limited imbibition that is insufficient for full hydration and seed germination. Alternatively, the same effect is achieved by mixing the seeds with hydrated absorbent medium such as clay or peat (e.g., U.S. Pat. No. 4,912,874). Controlled hydration with aqueous solutions may be achieved, for example, by utilizing semi-permeable membrane to mediate the transfer of water from a solution of a given osmotic pressure to the seed (U.S. Pat. No. 5,992,091). Priming is performed under a variety of temperatures and aeration methods (e.g., stirring, agitation, bubbling, etc.) using any of the techniques for controlled water uptake (Taylor A G. et al. 1998. Seed Science Technology 8:245-256).

Combination between the common transformation techniques described hereinabove and seed priming has been disclosed. For example, U.S. Pat. No. 6,646,181 discloses a method of introducing genes into plants comprising synchronizing the stage of development of the plant at a stage that includes large amounts of 4C DNA in seeds of the plants and transfecting the cells of the seeds, in which synchronizing the stage of development comprises admixing a particulate solid matrix material and a seed priming amount of water, with aeration of seeds, for a time and at a temperature sufficient to cause a substantial number of the cells of the seeds to reach a desired stage of a cell cycle.

U.S. Patent Application Publication No. 2006/0005273 discloses maize explants suitable for transformation. The explants comprise a maize seed split in half longitudinally, wherein the splitting exposes the scutellum, the coleoptilar ring and shoot apical meristem, each of which are independently suitable for transformation. Priming the seed prior to splitting with either callus or shoot priming medium increases the callus and shoot induction frequency after transformation.

U.S. patent application Ser. No. 20100154083 discloses compositions and methods to screen, identify, select, isolate, and/or regenerate targeted integration events using seed priming. Seed priming provides the identification of a seed having stably incorporated into its genome a site-specific recombinase mediated integration of a selectable marker at a target locus operably linked to a promoter active in the seed.

These combination methods employ the known methods of transformation and are aimed at increasing the efficacy of foreign gene integration into the plant genome. As described hereinabove, the available methods have limitations with regard to applicability and efficacy. In addition integration of the foreign DNA to the plant genome is not always desirable.

There is a recognized need for, and it would be highly advantageous to have means and methods for simple and efficient introduction of DNA into plant cells that further enable efficient plant regeneration.

SUMMARY OF THE INVENTION

The present invention provides means and methods for simple and efficient delivery of heterologous DNA into a plant cell, part, tissue, organ, or the entire organism, particularly to the cells of a seed embryo within an intact seed. The seed comprising the introduced heterologous DNA is easily grown to a mature plant under standard growth conditions, without the need of regeneration cultures and hardening conditions.

The present invention is based in part on the unexpected discovery that introduction of heterologous DNA into plant seeds is possible during seed priming by supplementing the priming medium with a virus-based DNA construct, particularly with a Geminivirus based expression construct. As exemplified hereinbelow, the present invention now shows that supplementing a priming medium with a Geminivirus based construct designated IL-60, which comprises the heterologous polynucleotide sequence flanked by non-contiguous nucleic acid sequences encoding a Geminivirus replicase or replicase associated proteins, result in the uptake, replication and symptomless spreading of the DNA construct within the seed cells.

The teachings of the present invention are advantageous over previously known methods for plant cell transformation or introduction of foreign DNA in that the DNA is introduced into the embryo of the intact seed which is naturally capable of developing into a whole plant. The teachings of the present invention for DNA introduction does not involve damage to the cells (as occurs when direct DNA transfer, particularly via bombardment is employed) or cell functioning. Furthermore, when Geminivirus-based expression constructs are employed, the heterologous DNA is not incorporated into the plant genome, again preventing the trauma accompanying DNA introduction into the cell which typically leads to cell cycle arrest and apoptosis or programmed cell death. The simple methods of the present invention can be employed with seeds of any plant of interest, and is fast and highly efficient. When the DNA construct used is such that the heterologous DNA does not incorporate into the plant genome, the method is further advantageous as the plant expresses the desired product but is not defined as genetically modified.

Thus, according to one aspect, the present invention provides a method for introducing heterologous DNA into at least one cell of a plant seed embryo comprising contacting a plant seed with a priming medium containing a virus-based DNA construct comprising the heterologous DNA under conditions enabling priming, thereby obtaining the seed embryo comprising the heterologous DNA.

According to certain embodiments, the method further comprises the step of providing suitable conditions for subsequent seed germination and growth so as to obtain a plant or part thereof comprising the heterologous DNA.

According to certain embodiments, the virus-based DNA construct comprises viral genes or parts thereof enabling replication and symptomless spreading of the construct into adjacent plant cells.

According to typical embodiments, the DNA construct is a Geminivirus based construct. According to these embodiments, the construct comprises the heterologous DNA flanked by a non-contiguous nucleic acid sequences encoding Geminivirus replicase or replicase-associated protein.

According to other embodiments, the construct further comprises a polynucleotide sequence encoding a modified Geminivirus coat protein (CP). According to typical embodiments, the modified Geminivirus coat protein encoding polynucleotide comprises a mutation or deletion in nucleotides encoding the N-terminal 100 amino acids.

According to further typical embodiments the expression construct further comprises a polynucleotide sequence encoding a modified Geminivirus V2 protein.

According to additional typical embodiments the expression construct further comprises a polynucleotide sequence encoding a modified Geminivirus C4 protein. According to these embodiments, the modified Geminivirus C4 protein includes a mutation or deletion. According to certain embodiments the expression construct further comprises a bacterial polynucleotide sequence.

According to certain currently preferred embodiments, the Geminivirus is Tomato Yellow Leaf Curl Virus (TYLCV). According to these embodiments, the Geminivirus-based construct is selected from the group consisting of IL-60 having the nucleic acids sequence set forth on SEQ OD NO:1 and IL-60-BS having the nucleic acids sequence set forth in SEQ ID NO:2.

According to certain embodiments, the DNA construct is designed as an expression construct such that the heterologous DNA is expressed in the plant cell. According to these embodiments, the DNA construct further comprises at least one regulatory element selected from the group consisting of an enhancer, a promoter, and a transcription termination sequence.

According to additional embodiments, the DNA construct further comprises a marker for identifying the seeds and/or plants comprising the heterologous DNA.

The heterologous DNA can encode any desired product, including peptides, polypeptide, proteins and RNAs. The proteins or RNAs can be of plant origin or of other origin, including but not limited to bacterial and mammal origin. According to certain embodiments, the DNA encodes an inhibitory RNA selected from the group consisting of antisense RNA, dsRNA, siRNA and the like, such that the expression of a target gene is silenced. According to other embodiments, the heterologous DNA encodes a product the expression of which confers a desirable agronomic trait including, but not limited to, resistance to biotic or a-biotic stress, increased yield, increased yield quality, preferred growth pattern and the like. According to additional embodiments, the encoded protein products are useful in the cosmetic or pharmaceutical industry. According to still further embodiments, the encoded protein enhances the production of desired metabolites within the plant cells and tissues.

According to yet other embodiments the heterologous DNA dose not encode a desired product but is present merely as a label to the origin of the seed, or to the plant grown from said seed, for example to prevent illegal distribution of proprietary seeds, plants and tissues.

The heterologous DNA may be transiently expressed in the cells and cells derived therefrom or it may be incorporated into the cell genome. The heterologous DNA may be present in the cytoplasm of the plant cell, in its organelles or in the nucleolus as an integrated or non-integrated DNA sequence.

According to certain currently preferred embodiments the DNA construct is a Geminivirus-based construct designed such that the heterologous DNA is not incorporated into the cell genome but the construct is capable of replicating and spreading within the cells of the plant grown from the seed comprising said heterologous DNA.

Any priming system and conditions as is known to a person skilled in the art can be used according to the teachings of the present invention, including systems comprising aqueous solutions with adequate osmotic potential and systems comprising solid particulates. The water potential of the medium enables water uptake that is insufficient for complete seed imbibitions, and allows only the initial stages of germination but not radicle emergence (completion of germination). The system and conditions are typically selected according to the species of the plant seed.

According to yet additional embodiments, the present invention provides a seed produced by the methods of the invention, the seed comprises a virus-based DNA construct comprising heterologous DNA, and plants or parts thereof produced from said seed.

According to certain embodiments, the plant seed is of a monocot origin. According to other embodiments, the plant seed is of a dicot origin.

Other objects, features and advantages of the present invention will become clear from the following description and drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 is an illustration of the Geminivirus based constructs used in the seed priming experiments described herein.

DETAILED DESCRIPTION OF THE INVENTION

Definitions

Figure 1:
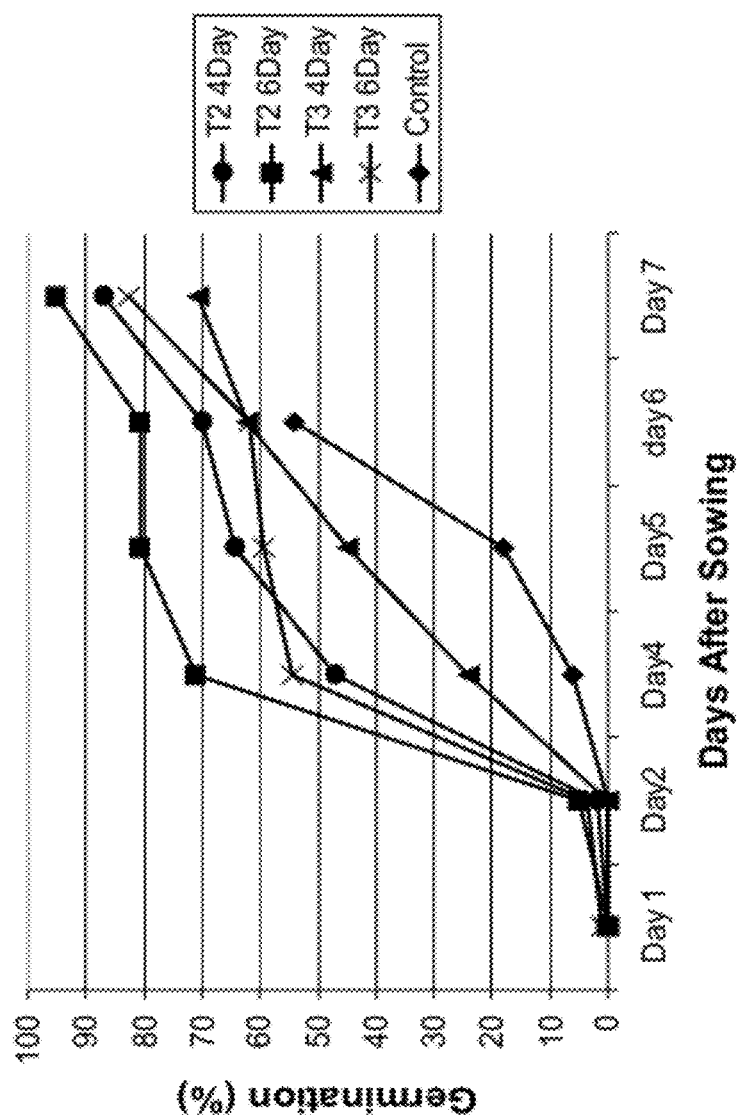
FIG. 1 demonstrates the effect of seed priming on germination uniformity.

The term "priming" as used herein refers to the pre-sowing restricted hydration treatment of seeds to improve germination and seedling establishment and to the biochemical, physiological and biological processes occurring within the seed prior to full hydration and germination. The priming process controls and manipulates the water availability to the seeds such that water availability suffice to initiate and affect the early events of germination, but is not sufficient to permit radicle emergence. Depending of the plant species and growers requirements, the above-described controlled hydration is subsequently followed by partial or complete drying, such that the seeds can be further stored for short or long time periods until sowing.

As used herein, the term "priming medium" refers either to solutions (inorganic, e.g., salts/nutrients, or organic, e.g., PEG) or to solid particulate systems (for example comprising kaolin) resulting in controlled hydration with water. Examples of such mediums are specified in. Taylor G P. et al. (1998. Seed Science Technology 8:245-256).

The term "conditions enabling priming" refers to suitable conditions of medium composition (e.g. osmotic PEG or other components solutions, solid water absorbents, and more); duration; temperatures; light/dark regimes; and aeration (e.g., stirring, agitation, bubbling, etc.) to induce seed priming using any technique as is known in the art for controlled water uptake.

The term "treated plants" refers to plants into which the heterologous DNA has been introduced, regardless if it has been integrated into the plant genome, into its organelles, or remained free in the cytoplasm, or resided as an episome in the nucleus without integration.

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, any storage organ (e.g., tuber, bulb, corm, false stem, leaves etc). The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be within the plant, in organ culture, tissue culture, or cell culture. The term "plant part" as used herein refers to a plant organ or a plant tissue.

The term "gene" refers to a nucleic acid (e.g., DNA or RNA) sequence that comprises coding sequences necessary for the production of RNA or a polypeptide. The term comprises natural as well as man tailored (synthetic) genes. A polypeptide can be encoded by a full-length coding sequence or by any part thereof. The term "parts thereof" when used in reference to a gene refers to fragments of that gene ranging in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either. The sequences which are located 5' of the coding region and which are present on the mRNA are referred to as 5' non-translated (or untranslated) sequences (5' UTR). The sequences which are located 3' or downstream of the coding region and which are present on the mRNA are referred to as 3' non-translated (or untranslated) sequences (3' UTR).

The term "nucleic acid" as used herein refers to RNA or DNA that is linear or branched, single or double stranded, or a hybrid thereof. The term also encompasses RNA/DNA hybrids.

The terms "heterologous DNA" or "exogenous DNA" refer to a polynucleotide that is not present in its natural environment (i.e., has been altered by the hand of man). For example, a heterologous DNA includes a polynucleotide from one species introduced into another species. A heterologous DNA also includes a polynucleotide native to an organism that has been altered in some way (e.g., mutated, added in multiple copies, linked to a non-native promoter or enhancer sequence, etc.). Heterologous DNA may comprise gene sequences of plants bacteria and mammal origin. The gene sequences may comprise cDNA forms of a gene; the cDNA sequences may be expressed in either a sense (to produce mRNA) or anti-sense orientation (to produce an anti-sense RNA transcript that is complementary to the mRNA transcript). Heterologous plant genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "construct" is used herein in its broad sense, referring to an artificially assembled or isolated nucleic acid molecule which includes the heterologous DNA interest. In general a construct may include the heterologous DNA, typically a gene of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or anti-sense orientation.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters". New promoters of various types useful in plant cells are constantly being discovered; numerous examples may be found in Okamuro J K and Goldberg R B (1989) Biochemistry of Plants 15:1-82.

As used herein, the term an "enhancer" refers to a DNA sequence which can stimulate promoter activity, and may be an innate element of the promoter or a heterologous element inserted to enhance the level or tissue-specificity of a promoter.

The term "expression", as used herein, refers to the production of a functional end-product e.g., an mRNA or a protein Preferred Modes for Carrying Out the Invention The present invention provides methods for introducing heterologous DNA into plant cells or tissue. The methods of the invention enable a simple, easy to use, inexpensive, widely accessible, and efficient way to produce seeds and plants comprising exogenous DNA. According to the methods of the invention the desired DNA is introduced into the seeds and then plants are grown from the seeds, thus increasing considerably the efficiency of DNA introduction and saving on the costly and sometimes difficult plant regeneration process.

According to one aspect, the present invention provides a method for introducing heterologous DNA into at least one cell of a plant seed embryo comprising contacting the plant seed with a priming medium containing a virus-based DNA construct comprising the heterologous DNA under conditions enabling priming, thereby obtaining a seed embryo comprising the heterologous DNA.

According to certain embodiments, the virus-based DNA construct comprises viral genes or parts thereof enabling replication and symptomless spreading of the construct into adjacent plant cells.

According to certain embodiments, the method further comprises providing the suitable conditions for subsequent seed germination and growth so as to obtain a plant or part thereof comprising the heterologous DNA.

The term "comprising the heterologous DNA" when used in reference to a plant or seed refers to a plant or seed that contains at least one heterologous DNA in one or more of its cells. The term refers broadly to a plant, a plant structure, a plant tissue, a plant seed or a plant cell that contains at least one heterologous DNA in at least one of its cells. This term includes the primary cell to which the DNA was introduced and cultures and plants derived from that cell without regard to the number of transfers. All progeny may not be precisely identical in DNA content, due to deliberate or inadvertent mutations. Mutant progeny that have the same functionality as screened for in the originally cell to which the DNA was introduced are included in the definition of transformants.

Introduction of a heterologous DNA into a cell may be stable or transient. The term "transient" refers to the introduction of one or more exogenous polynucleotides into a cell in the absence of integration of the exogenous polynucleotide into the host cell's genome. This type of DNA introduction may be also referred to as "transient transformation". The term "transient transformant" thus refers to a cell which has transiently incorporated one or more exogenous polynucleotides. Transiently transformed cells are typically referred to as "non-transgenic" or "non-genetically modified (non-GMO)". In contrast, stable DNA introduction is referred to as "stable transformation" resulting in "stably transformed" cell or tissue and refers to the introduction and integration of one or more exogenous polynucleotides into the genome of a cell. The term "stable transformant" refers to a cell which has stably integrated one or more exogenous polynucleotides into the genomic or organellar DNA (chloroplast and/or mitochondria). Plants or parts thereof comprising cell stably transformed with exogenous DNA are typically referred to as "transgenic plants", "transgenic plant cell" or, in the context of the present invention "transgenic seeds".

The virus-based DNA construct of the present invention is capable of systemic, symptomless spread in the plant to which it was introduced. As used herein, the term "systemic, symptomless spread" refers to the ability of the virus-based vector to spread, for example, from the embryo cell to the developing leaf cells, without inducing the characteristic pathogenic symptoms of the virus. The DNA construct may be further transmitted to the offspring of the plant comprising the heterologous DNA. Without wishing to be bound by any specific theory or mechanism of action, such transfer may result from the spreading of the virus-based DNA construct into the plant reproductive cells.

According to certain currently preferred embodiment, the DNA construct is based on the Geminivirus genetic components, as disclosed in US Patent Application No. 20100071088 incorporated herein in its entirety by reference. The construct comprises the heterologous polynucleotide sequence flanked by a non-continuous nucleic acid sequences encoding a Geminivirus replicase.

According to other embodiments, the construct further comprises a polynucleotide sequence encoding a modified Geminivirus coat protein (CP). According to typical embodiments, the modified Geminivirus coat protein has the amino acid sequence set forth in SEQ ID NO:3. According to additional embodiments, the modified Geminivirus coat protein encoding polynucleotide comprises a mutation or deletion in nucleotides encoding the N-terminal 100 amino acids.

According to further typical embodiments the expression construct further comprises a polynucleotide sequence encoding a modified Geminivirus V2 protein. According to typical embodiments, the modified Geminivirus V2 protein has the amino acid sequence set forth in SEQ ID NO:4.

According to additional typical embodiments the expression construct further comprises a polynucleotide sequence encoding a modified Geminivirus C4 protein. According to typical embodiments, the modified Geminivirus C4 protein has the amino acid sequence set forth in SEQ ID NO:5. According to these embodiments, the modified Geminivirus C4 protein includes a mutation or deletion.

It is to be explicitly understood that other virus-based construct carrying long heterologous polynucleotides and capable of replicating and symptomless spread are also encompassed within the teachings of the present invention. As used herein, the term "long heterologous polynucleotides" refers to polynucleotides at least 1 kb long, typically at least 5 kb long more typically 6 kb long.

According to certain typical embodiments, the DNA construct is based on the tomato yellow leaf curl virus (TYLCV). Examples of such constructs are IL-60-BS (having the nucleic acid sequence set forth in SEQ ID NO:2) and pIR-GUS (having the nucleic acid sequence set forth in SEQ ID NO:8) as described in FIG. 2.

The Geminivirus based construct used according to the teachings of the present invention are introduced into the seed embryo cells, and are not integrated into the genome of the cells. The plant grown from the seed comprising the heterologous DNA and the plant grown therefrom are thus referred to as non-genetically modified plant.

The agricultural use of genetically-modified plants is a matter of public debate and in many countries is unacceptable by law or regulation. The main considerations voiced against the use of transgenic plants are the fear of inappropriate selection of a transgenic lineage (due to masked deleterious positional effects), possible cross-fertilization with weeds and other crops, further genome alterations due to recombination (especially when copies of endogenous genes are added) and possible transduction of the foreign sequences to plant and soil microorganisms. Introduction of antibiotic-resistant genes to food and the environment is also a major concern.

Bio-safety and environmental aspects can only be concluded upon following actual, carefully controlled, field tests over time. Clearance to conduct such experiments depends on evaluation based on hard laboratory data. One advantage of the methods of the present invention arises from the finding that the TYCLV based constructs appear to be environmentally-friendly and ready for bio-safety-evaluation field tests. Geminiviruses are not seed-transmissible (Kashina et al. 2003. Phytoparasitica 31:188-199). The vector forms IL-60-BS and pIR are not insect-transmissible even when the plants were colonized with a large number of insect vectors. Thus, the TYCLV based constructs are highly suitable for plant transformation.

The presence of the heterologous DNA in the cell of a treated seed, whether expressed transiently or stably integrated, can be verified by employing any suitable method as is known to a person skilled in the art. Stable transformation of a cell may be detected by isolating genomic DNA and employing Southern blot hybridization with nucleic acid sequences which are capable of binding to one or more of the exogenous polynucleotides or employing polymerase chain reaction with appropriate primers to amplify exogenous polynucleotide sequences. Expression of the transformed DNA can be detected by for example, enzyme-linked immunosorbent assay (ELISA), which detects the presence of a polypeptide encoded by one or more of the exogenous polynucleotides or by detecting the activity of the protein encoded by the exogenous polynucleotide.

Alternatively, the exogenous DNA can comprise a marker. A marker provides for the identification and/or selection of a cell, plant, and/or seed expressing the marker. A marker can encode a product, which when expressed at a sufficient level, confers resistance to a selective agent. Such markers and their corresponding selective agents include, but are not limited to, herbicide resistance genes and herbicides; antibiotic resistance genes and antibiotics; and other chemical resistance genes with their corresponding chemical agents. Bacterial drug resistance genes include, but are not limited to, neomycin phosphotransferase II (nptII) which confers resistance to kanamycin, paromycin, neomycin, and G418, and hygromycin phosphotransferase (hph) which confers resistance to hygromycin B. Resistance may also be conferred to herbicides from several groups, including amino acid synthesis inhibitors, photosynthesis inhibitors, lipid inhibitors, growth regulators, cell membrane disrupters, pigment inhibitors, seedling growth inhibitors, including but not limited to imidazolinones, sulfonylureas, triazolopyrimidines, glyphosate, sethoxydim, fenoxaprop, glufosinate, phosphinothricin, triazines, bromoxynil, and the like.

Additional type of marker is a marker the expression of which can be detected by following a biochemical reaction preferably producing color, upon providing of an appropriate substrate. Examples are the GUS (beta-glucuronidase) reporter system, luciderin-luciferase, green-fluorescent protein (GFP) system and the like.

According to certain embodiments, the DNA construct further comprises a regulatory element including, but not limited to, a promoter, an enhancer, and a termination signal.

Among the most commonly used promoters are the nopaline synthase (NOS) promoter (Ebert et al., 1987 Proc. Natl.

Acad. Sci. U.S.A. 84:5745-5749), the octapine synthase (OCS) promoter, caulimovirus promoters such as the cauliflower mosaic virus (CaMV) 19S promoter (Lawton et al., 1987 Plant MoI Biol. 9:315-324), the CaMV 35S promoter (Odell et al., 1985 Nature 313:810-812), and the figwort mosaic virus 35S promoter, the light inducible promoter from the small subunit of rubisco, the Adh promoter (Walker et al., 1987 Proc. Natl. Acad. Sci. U.S.A. 84:6624-66280), the sucrose synthase promoter (Yang et al., 1990 Proc. Natl. Acad. Sci. U.S.A. 87:4144-4148), the R gene complex promoter (Chandler et al., 1989 Plant Cell 1:1175-1183), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. 1982 Cell 29:1015-1026). A plethora of promoters is described in International Patent Application Publication No. WO 00/18963.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L. et al. (1989. Plant Cell 1:671-680).

The method of the present invention can be used for introducing any polynucleotide the presence and/or expression of which is of interest, including giving the plant desired property(ies) such as (a) resistance to biotic and a-biotic stress conditions, e.g., to insects, nematodes, diseases caused by viral, bacterial fungal and other pathogens pests, resistance to specific herbicide(s) (b) adaptation to hostile conditions such as salt tolerance, drought tolerance, cold and heat tolerance; (c) improved yield quality traits, including but not limited to pigmentation, firmness, type and content of ingredients including sugars, volatiles, oils, fatty acids and/or acids, size, growth rate, dwarf growth habit, time of emergence, time of fruit appearance and ripening; nutritional or commercial value; (d) improved production of edible yields, or of secondary metabolites, for the biopharmaceutical and cosmetic industries either in the form of a protein, secondary metabolites and (e) obtaining a desired growth habit, including determinate, semideterminate and indeterminate (e.g. for tomato), dwarf and normal (e.g. for corn) and plant vigor. The introduced DNA can also confer gene silencing such that the heterologous DNA is in the form of antisense, siRNA, dsRNA; or for producing raw materials for industries, including but not limited to fiber, wood, oils, resins, etc. as well as other plant traits governed by genetic factors, and/or interaction by genes and environment.

The expressed polynucleotide sequence can encode a molecule which would protect the plant from abiotic stress factors such as drought, heat or chill. Examples include antifreeze polypeptides from *Myoxocephalus Scorpius* (WO 00/00512) or *M. octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580), ferritin (Deak M. et al. 1999. Nature Biotechnology 17:192-196), oxalate oxidase (WO 99/04013), DREBIA factor (Kasuga M. et al. 1999. Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

The expressed polynucleotide sequence could be a metabolic enzyme for use in the food-and-feed sector. Examples include phytases (GenBank Ace. No.: A 19451) and cellulases.

The expressed polynucleotide sequence can confer resistance to viruses, fungi, insects, nematodes and other pathogens and diseases, by directly attacking the pathogen, turning on the host defenses or by leading to an accumulation of certain metabolites or proteins. Examples include glucosinolates (defense against herbivores), chitinases or glucanases and other enzymes which destroy the cell wall of parasites, ribosome-inactivating proteins (RIPS) and other proteins of the plant resistance and stress reaction as are induced when plants are wounded or attacked by microbes, or chemically, by, for example, salicylic acid, jasmonic acid or ethylene, or lysozymes from non-plant sources such as, for example, T4-lysozyme or lysozyme from a variety of mammals, insecticidal proteins such as *Bacillus thuringiensis* endotoxin, α-amylase inhibitor or protease inhibitors (cowpea trypsin inhibitor), lectins such as wheatgerm agglutinin, siRNA, antisense RNA, RNAses or ribozymes. Further examples are nucleic acids which encode the *Trichoderma harzianum* chit42 endochitinase (GenBank Ace. No.: S78423) or the N-hydroxylating, multi-functional cytochrome P-450 (CYP79) protein from *Sorghum bicolor* (GenBank Ace. No.: U32624), or functional equivalents thereof.

Resistance to pests such as, for example, the rice pest *Nilaparvata lugens* in rice plants can be achieved by expressing the snowdrop (*Galanthus nivalis*) lectin agglutinin (Rao et al. 1998. Plant J 15(4):469-77).

The expression of synthetic cryIA(b) and cryIA(c) genes, which encode lepidoptera-specific *Bacillus thuringiensis* delta-endotoxins can bring about a resistance to insect pests in various plants (Goyal R K. et al. 2000. Crop Protection 19(5):307-312).

Additional genes which are suitable for pathogen defense comprise "polygalacturonase-inhibiting protein" (PGIP), thaumatine, invertase and antimicrobial peptides such as lactoferrin (Lee T J. et al. 2002. J Amer Soc Horticult Sci 127(2):158-164). The expressed polynucleotide sequence can bring about an accumulation of chemicals such as of tocopherols, tocotrienols or carotenoids. One example of such a polynucleotide is phytoene desaturase. Preferred are nucleic acids which encode the Narcissus pseudonarcissus phytoene desaturase (GenBank Ace. No.: X78815) or functional equivalents thereof. The expressed polynucleotide sequence can be used for production of nutraceuticals such as, for example, polyunsaturated fatty acids (arachidonic acid, eicosapentaenoic acid or docosahexaenoic acid) by fatty acid elongases and/or desaturases, or for production of proteins with improved nutritional value such as, for example, with a high content of essential amino acids (for example the high-methionine 2S albumin gene of the brazil nut). Preferred are polynucleotide sequences which encode the *Bertholletia excelsa* high-methionine 2S albumin (GenBank Ace. No.: AB044391), the *Physcomitrella patens* delta-6-acyl-lipid desaturase (GenBank Ace. No.: AJ222980), the *Mortierella alpina* delta-6-desaturase (Sakuradani et al. 1999. Gene 238: 445-453), the *Caenorhabditis elegans* delta-5-desaturase (Michaelson et al. 1998, FEBS Letters 439:215-218), the *Caenorhabditis elegans* A5-fatty acid desaturase (des-5) (GenBank Ace. No.: AF078796), the *Mortierella alpina* delta-5-desaturase (Michaelson et al. JBC 273: 19055-

19059), the *Caenorhabditis elegans* delta-6-elongase (Beaudoin et al. 2000. PNAS 97:6421-6426), the *Physcomitrella patens* delta-6-elongase (Zank et al. 2000. Biochemical Society Transactions 28:654-657), or functional equivalents of these.

The expressed polynucleotide sequence can be used for production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described, for example, by Hood E E. et al. (1999. Curr Opin Biotechnol 10(4):382-60 and Ma J K. et al. (1999. Curr Top Microbiol Immunol 236:275-92). For example, it has been possible to produce recombinant avidin from chicken albumen and bacterial P-glucuronidase (GUS) on a large scale in transgenic maize plants (Hood et al. 1999. Adv Exp Med Biol 464: 127-47; Review).

The expressed polynucleotide sequence can be also used for obtaining an increased storability in cells which normally comprise fewer storage proteins or storage lipids, with the purpose of increasing the yield of these substances for example acetyl-CoA carboxylase. Preferred polynucleotide sequences are those which encode the Medicago sativa acetyl-CoA carboxylase (accase) (GenBank Ace. No.: L25042), or functional equivalents thereof.

Additional examples of expressible polynucleotides include Hepatitis B surface antigen (Kumar G B S et al. 2005. PLANTA 222 (3):484-493), herbicide resistance (Duke, S 0.2005. Pest Management Science 61(21):1-218), interferon (Edelbaum, O. et a1.1992. J. Interferon Res. 12:449-453), T7-RNA polymerase (Zeitoune et al. 1997. Plant Science 141:59-65).

Further examples of polynucleotide sequence which can be expressed in the transformed plants of the present invention are mentioned for example in Dunwell J M. 2000. J Exp Bot. 51:487-96.

The heterologous DNA transformed into the plant cell according to the teachings of the present invention can also be employed for the reduction (suppression) of transcription and/or translation of target genes. Thus, the DNA construct can comprises heterologous DNA the expression of which brings about PTGS (post transcriptional gene silencing) or TGS (transcriptional silencing) effects and thus a reduction of the expression of endogenous genes. Such reduction can be achieved for example by expression of an antisense RNA or of a double-stranded RNA, each of which has homology with the endogenous target gene to be suppressed. Also, the expression of a suitable sense RNA can cause a reduction in the expression of endogenous genes, by means of what is known as co-suppression (EP Application Publication No. 0465572). Particularly preferred is the expression of a double-stranded small interfering RNA (siRNA) for reducing the gene expression of a target gene via RNA interference (RNAi). Methods for inhibiting individual target genes using RNA with double-stranded structure, where the target gene and the region of the RNA duplex have at least partial identity are known to a person skilled in the art.

The following provide examples for applications where reduction of gene expression can be obtained by transforming plant seed with an appropriate heterologous DNA according to teachings of the present invention.

Delayed fruit maturation or a modified maturation phenotype (prolonged maturation, later senescence) can be achieved for example by reducing the gene expression of genes selected from the group consisting of polygalacturonases, pectin esterases, β-1,4)glucanases (cellulases), β-galactanases (β-galactosidases), or genes of ethylene biosynthesis, such as 1-aminocyclopropane-1-carboxylate synthase, adenosylmethionine hydrolase (SAMase), aminocyclopropane-1-carb-oxylate deaminase, aminocyclopropane-1-carboxylate oxidase, genes of carotenoid biosynthesis such as, for example, genes of pre-phytoene biosynthesis or phytoene biosynthesis, for example phytoene desaturases, and O-methyltransferases, acyl carrier protein (ACP), elongation factor, auxin-induced gene, cysteine(thiol) proteinases, starch phosphorylases, pyruvate decarboxylases, chalcone reductases, protein kinases, auxin-related gene, sucrose transporters, meristem pattern gene. Further advantageous genes are described for example in International (PCT) Applications Publication Nos. WO 91/16440, WO 91/05865, WO 91/16426, WO 92/17596, WO 93/07275 or WO 92/04456. particularly preferred is the reduction of the expression of polygalacturonase for the prevention of cell degradation and mushiness of plants and fruits, for example tomatoes. Nucleic acid sequences such as that of the tomato polygalacturonase gene (GenBank Acc. No.: x14074) or its homologs can preferably used for this purpose.

The reduction of the gene expression of genes encoding storage proteins has numerous advantages, such as, for example, the reduction of the allergenic potential or modification regarding composition or quantity of other metabolites, such as, for example, oil or starch content.

Resistance to plant pathogens such as arachnids, fungi, insects, nematodes, protozoans, viruses, bacteria and diseases can be achieved by reducing the gene expression of genes which are essential for the growth, survival, certain developmental stages (for example pupation) or the multiplication of a specific pathogen. Such a reduction can bring about a complete inhibition of the abovementioned steps, or else a delay of same. They can take the form of plant genes which for example make possible the penetration of the pathogen, but may also be homologous pathogen genes. The transformed and expressed heterologous nucleic acid sequence (for example the double-stranded RNA) is directed against genes of the pathogen, such that the pathogen life cycle is interrupted.

Virus resistance can be achieved for example by reducing the expression of a viral coat protein, a viral replicase, a viral protease and the like. A large number of plant viruses and suitable target genes are known to the skilled artisan.

Reduction of undesired, allergenic or toxic plant constituents such as, for example, glucosinolates or patatin. Suitable target genes are described (in WO 97/16559, inter alia). The target genes which are preferred for reduction of allergenic proteins are described for example by Tada Y et al. (1996) FEBS Lett 391(3):341-345 or Nakamura R (1996) Biosci Biotechnol Biochem 60(8):1215-1221.

Delayed signs of senescence. Suitable target genes are, inter alia, cinnamoyl-CoA:NADPH reductases or cinnamoyl-alcohol dehydrogenases. Further target genes are described (in WO 95/07993, inter alia).

Increase of the methionine content by reducing threonine biosynthesis, for example by reducing the expression of threonine synthase (Zeh M et al. 2001. Plant Physiol 127(3): 92-802).

A plant seed is a complete self-contained reproductive unit generally consisting of a zygotic embryo resulting from sexual fertilization or through asexual seed reproduction (apomixis), storage reserves of nutrients in structures referred to as cotyledons, endosperm or megagametophytes, and a protective seed coat encompassing the storage reserves and embryo. In nature, maturation of plant seeds is usually accompanied by gradual loss of water over a period of time to levels between 5-35% moisture content. Once these low moisture levels are achieved, plant seeds can be stored for extended periods.

Germination of sexual zygotic and apomictic plant seeds is generally triggered by one or more environmental cues such as the presence of water, oxygen, optimal temperature or cold/hot treatment, and exposure to light and its duration. Seeds germinate by means of a series of events which commence with the uptake of water (imbibition) by a quiescent dry seed and then subsequently proceed through various biophysical, biochemical and physiological events which ultimately result in the elongation of the embryo along its axis and development of the offspring.

The continuous process of seed germination may be divided into three phases. Phase one is referred to as imbibition and is characterized by a rapid initial intake of water into the seed. Other significant events occurring in phase one are the initiation of repair of damage nuclear and mitochondrial DNA, which may have occurred during seed desiccation and/or the maturation process, and subsequent commencement of protein synthesis facilitated by existing mRNA.

Phase two is characterized by a significant reduction in the rate of water uptake (i.e., imbibition has been completed). This is accompanied by activation or de novo synthesis of enzymes that specialize in hydrolyzing the complex storage reserves of carbohydrates, proteins, and lipids in the embryo and the cotyledons or megagametophytes. The hydrolysis of these complex storage reserves provides the substrates required for the respiration and growth of the seed embryos.

Phase three is characterized by a second rapid increase in the rate of water uptake. Water absorbed during phase three is used primarily for the initiation of meristematic cell division at the root and shoot apices of the embryo, and for uptake into the cells along the embryonal axis. Water taken up by the axial cells of the embryo applies turgor pressure which results in axial cell elongation. The net effect is that the embryo elongates to the point of emergence through the seed coat. Protrusion of a shoot or root radicle through the seed coat signifies the completion of germination and the onset of seedling growth and development.

The speed and success for germination of seeds varies considerably depending on various factors such as the residual influence of environmental conditions in which the seed developed and maturated, the amount of storage reserve compounds synthesized during the seed maturation process, the duration of storage, the quality of the storage environment (e.g., temperature and humidity) and the environmental conditions prevailing during the germination processes. From a commercial perspective, it is desirable to reduce the risk of germination failure and to ensure that seeds emerge and germinate rapidly and uniformly.

The commercial need for optimum seed germination performance has led to the development of processes known in the art for zygotic seeds as "seed priming". This term may be defined as the limited uptake of water that is sufficient to initiate the early events of germination, but not sufficient to permit radicle protrusion, preferably followed by drying. Several principle techniques are used commercially to accomplish seed priming. Regardless of the particular method used, the fundamental principles of seed priming are that: (1) the preliminary stages of germination are activated specifically and exclusively through controlling the availability of water to the seeds, and (2) the germination processes initiated through an external priming process are subsequently arrested by a desiccation or partial desiccation step.

Unexpectedly, the present invention now shows that including a virus-based DNA construct in the seed priming medium results in the uptake of the DNA by the seed such that the DNA enters the seed cells. Without wishing to be bound by any specific theory or mechanism of action, this phenomenon may be attributed to viral elements enabling the introduction of the heterologous DNA into the seeds cells.

Any method for seeds priming as is known to a person skilled in the art can be used according to the teachings of the present invention. Priming can be performed under a variety of temperatures and aeration (e.g., stirring, agitation, bubbling, etc.) using any of the techniques for controlled water uptake: priming with solutions (inorganic, e.g., salts/nutrients, or organic, e.g., PEG) or with solid particulate systems or by controlled hydration with water as described, for example, in Taylor, A G. et a11998. Seed Science Technology 8:245-256).

A priming matrix is characterized by its effective osmotic potential. An effective osmotic potential typically lowers the water potential available for seed imbibitions allowing or causing a limited amount of water to move into the seed to a level sufficient for initial steps of germination without actual protrusion of the radical, i.e., to prime the seed. Seeds germination occurs only when water available to the seed reaches a potential sufficient for physiological development, which varies between plant species. Typically this value falls between 0 and −2 mPa. Many priming matrices that provide an appropriate osmotic potential are being used, including water, water with one or more solutes, solid matrices, and the like. For example, the priming matrix may comprise an aerated solution of osmotic material, of organic nature such as polyethylene glycol (PEG) (see U.S. Pat. No. 5,119,598), glycerol, mannitol, or inorganic salt (or combination of salts) such as potassium phosphate, potassium nitrate, and the like. Alternatively, seeds may be primed using a solid matrix. A solid matrix material should have a high water holding capacity to allow seeds to imbibe. In this method, the priming matrix can comprise an absorbent medium such as clay, vermiculite, perlite, saw dust, corn cobs, and/or peat to absorb water and then transfer it to the seed (e.g., U.S. Pat. No. 4,912,874). The extent of hydration is controlled by altering the water content of the medium and the medium/seed ratio. Methods are also known to imbibe seeds in a slurry of PEG 6000 and vermiculite, or other matrices (e.g., U.S. Pat. No. 5,628,144). In still other methods, priming employs a semipermeable membrane that mediates the transfer of water from a solution characterized by a given osmotic pressure to the seed (e.g., U.S. Pat. No. 5,873,197). In other methods, ultrasonic energy can be used to assist in the priming process (e.g., U.S. Pat. No. 6,453,609). Optionally a variety of additives, chemicals, and/or compounds can be included in the priming matrix, including surfactants, selective agents, fungicides, agents to modify osmotic potential, osmotic protectants, agents to aid drying or protect the seed during drying, agents to enhance seed processing, agents to extend storage shelf-life, agents to enhance coating and/or perfusion, agents to enhance germination of the seed, and the like. Fungicides can be included in the priming matrix, for example, thiram, captan, metalaxyl, pentachloronitrobenzene, fenaminosulf, bactericides or other preservatives. In addition, various growth regulators or hormones, such as gibberellins or gibberellic acid, cytokinins, inhibitors of abscissic acid, 2-(3,4-dichlorophenoxy) triethylamine (DCPTA), potassium nitrate, and ethaphon can also be present in the priming matrix. Other optional agents include glycerol, polyethylene glycol, mannitol, DMSO, Triton X-100, Tween-20, NP-40, ionic compounds, non-ionic compounds, surfactants, detergents, and the like. A time sufficient to produce a primed seed allows pre-germinative metabolic processes to take place within the seed up to any level including that immediately preceding radicle-emergence. The time to produce a primed seed is dependent on the specific seed variety, its state or condition, and the water potential of the priming matrix. While typical water amounts and media water potentials for given seed types are already generally known for some seeds, it is frequently best to test a small sample of a new seed over a readily determined range of osmotic potentials and temperatures to determine what conditions of temperature, water potential, and time provide appropriate imbibing of the seed and resultant pre-germination events. The temperature at which the priming methods are carried out may vary with the seeds to be treated, but typically is between 18° C. to 30° C. The primed seeds may be retained in the priming matrix through germination as denoted by radical emergence. Seed produced by this method may be further dried (e.g., as in U.S. Pat. No. 4,905,411).

Methods to determine if a seed has been primed are known in the art. For example, optimization of priming treatments can be performed by carrying out germination assays. (See, for example, Jeller H. et al. 2003. Braz J Biol 63:61-68). In addition, molecular markers of germination and/or priming are known. See, for example, Job et al. 2000. Seed Biology: Advances and Applications, Eds. Black et al., CABI International, Wallingford, UK, pp. 449-459; De Castro R D. et al. 2000. Plant Physiol 122:327-336; Bradford et al. 2000. Seed Biology: Advances and Applications, Eds. Black et al., CABI International, Wallingford, UK pp. 221-251; and Gallardo K. et al. 2001 Plant Physiol 126:835-848.

After priming, the seeds may be allowed to germinate, or the primed seeds can be dried. The appropriate conditions (temperature, relative humidity, and time) for the drying process will vary depending on the seed and can be determined empirically (see, for example, Jeller et al. 2003. ibid). Drying primed seed includes a superficial drying of the seed or, alternatively, drying the seed back to its original water content. The dried seeds can be immediately germinated or can be stored under appropriate conditions. Germination conditions for various seeds are known. One factor in determining appropriate germination conditions is the threshold germination temperature range, which is the range of temperatures for a species within which seeds of that species will germinate at a predetermined moisture level and with adequate oxygen. Another factor is the threshold germination moisture range, which is the range of moisture for a species within which seeds of the species will germinate at a given temperature and with adequate oxygen. Threshold germination temperature range and/or threshold germination moisture range values are known for various seeds, as are methods to empirically determine these conditions for any given seed and variety.

The method of the invention greatly reduces the time required for introduction of heterologous gene(s) into the plant cells, generation, selection and propagation of the plants of interest. The potential for somaclonal variation caused by tissue de-differentiation in culture is nullified. When Geminivirus-based construct is used, the plants contain foreign DNA, as every tissue infected with benign microorganisms does, and yet the treated plants are not genomically modified. The method of the invention can cut drastically the time and cost of breeding, since it facilitates the expression of gene(s) of interest in any desired plant variety, thus adding needed traits such as resistance/tolerance to biotic/a-biotic stress conditions, improving yield and quality for any given environment and market and the like, as long as genes controlling the desired trait are known. Similarly, the heterologous DNA introduced according to teachings of the present invention can result in silencing of certain process(es) when so required (e.g., development of green back in tomato fruit is desired in Italy but is unacceptable in the USA).

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Priming Using a Priming Medium without Foreign DNA

Tomato seed priming in the presence of polyethylene glycol (PEG) was carried out as previously described (Khan, A A. 1992. In: Horticultural Reviews, Vol. 14, ed. J. Janick. New York: John Wiley, pp. 131-181; Taylor G. et al. 1998. Seed Science Technology 8:245-256), with some modifications.

Batches of 50 tomato seeds were imbibed in a solution composed of 0.1M $Ca(NO_3)_2$; 0.1M MES (4-morpholineetahnsulfonic acid); 15 mM $MgCl_2$ and 25% (solution T2) or 20% (solution T3) of PEG 8000. The osmotic pressure of solutions T2 and T3 was −1.25 mPa and −1.2 mPa respectively. Untreated dry seeds of the same cultivar, same seed lot were used as control. Treatment was carried out under constant temperature of 20° C. with a 12 hour light regimen daily, and stirred gently for 4 or 6 days to obtain proper aeration. Seeds were then placed on 3M filter paper supplemented with 3 ml sterile water and germination rates were recorded daily. The data demonstrate (FIG. 1) a significant increase in germination uniformity of primed seed in comparison with control (successful priming).

Example 2

Introducing IL-60 Constructs into Seeds by Using Priming Medium

Figure 2A:
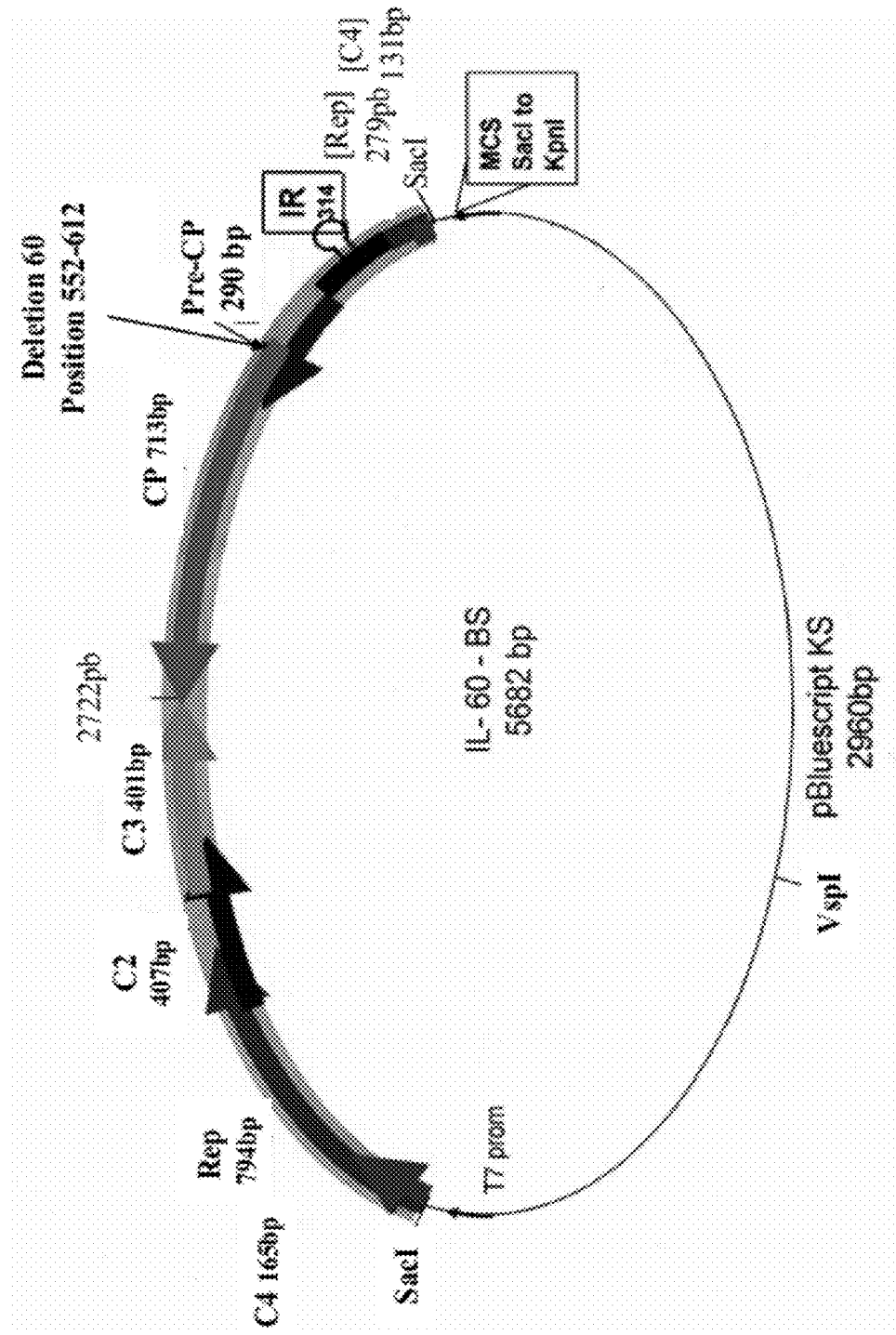
FIG. 2A: IL-60-BS.
Figure 2B:
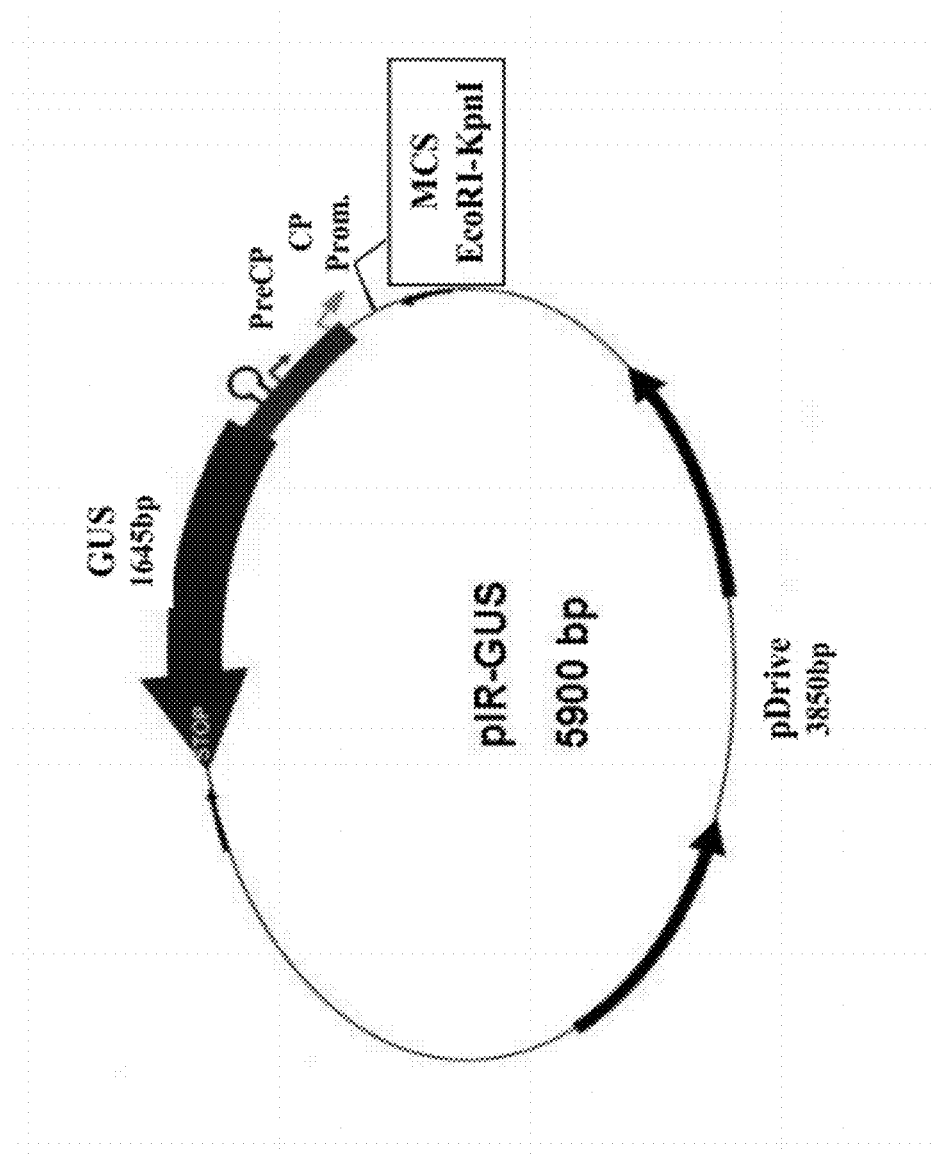
FIG. 2B: pIR-GUS.

Tomato seeds were primed with a priming solution containing 25% PEG and germinated as described in Example 1 above in the presence of 20, 40 and 60 μg of each of the IL-60-BS (SEQ ID NO:2) and pIR-GUS (SEQ ID NO:8) DNA constructs. The constructs are illustrated in FIG. 2A and 2B, respectively. Constructs are also described in US Patent Application No. 20100071088, incorporated herein by reference. Untreated dry seeds and seeds primed at the same conditions but without the DNA construct served as control.

Figure 3:
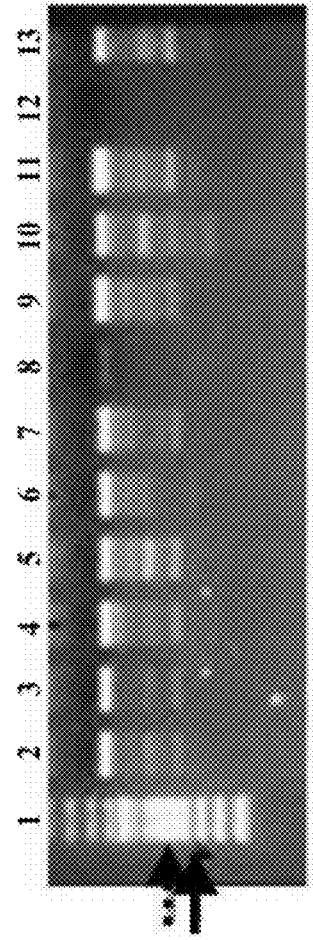
FIG. 3 shows the presence of GUS sequences in true tomato leaves following seed priming in the presence of the Geminivirus based constructs, detected by PCR. The dashed and solid arrows indicate the position of a size marker of 1,500 bp and the position of GUS (ca. 1,800 bp) respectively (lane 1). Lane 8 and 12 are negative controls: PCR from plants grown from non-treated seeds and from plant from seeds imbibed with no DNA construct, respectively.

Six days after germination the seedlings were transplanted into pots containing 10 liters soil and placed in a greenhouse at 25° C. Twenty one days after planting, DNA was extracted from true leaves (the third true leaf or above) and subjected to PCR with the following primers for GUS assay:

Forward primer: ATTGATCAGCGTTGGTGGGA (SEQ ID NO:6) and reverse primer: TGCGGTCGCGAGTGAAGATC (SEQ ID NO:7) designed to amplify the entire gus gene present within the pIR-GUS DNA construct. Positive PCR reaction confirmed the presence of a GUS DNA sequence in the true leaves. These results show that the DNA constructs of the IL-60 based vectors were introduced to the seed cell(s) using the above priming procedure. The introduced DNA replicated, spread and was expressed throughout the plant system. An example of the results of such assay is shown in FIG. 3.

Example 3

Expression of the Foreign Genes

The DNA constructs of the IL-60 family as detailed in Example 2 above (IL-60-BS in combination with pIR-GUS) facilitated the expression of the foreign gus gene present within the pIR-GUS DNA construct and introduced via priming.

Tomato leaves from the plant obtained as described in Example 2 above were stained for beta-glucuronidase (GUS) according to Jefferson R A. et al. (1987. EMBO J 6: 3901-3907).

Figure 4B:
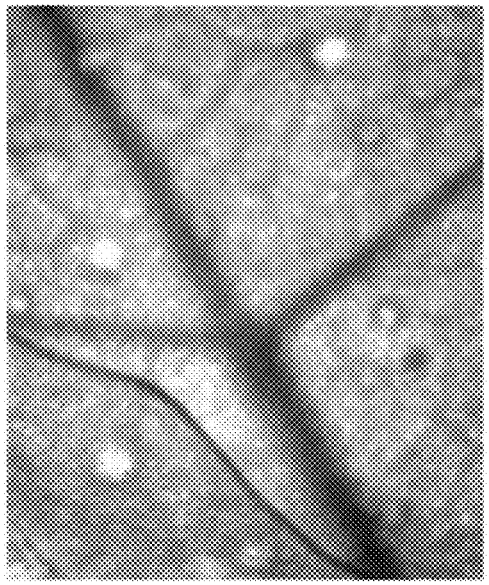
FIGS. 4A and 4B show cross sections of tomato leaves stained for GUS activity following seed priming in the presence of IL-60-BS and pIR-GUS (FIG. 4B mag. X40)
Figure 4A:

Blue color staining of the leaf tissue clearly denotes the expression of the GUS protein (FIG. 4A-B).

Example 4

Expression of Specific DNA from IL-60 Vectors Under Modified Priming Conditions Priming was conducted as in example 2 with the basic priming solution containing 5% PEG and the addition of 75% dimethylsulfoxide (DMSO) as to obtain final osmotic potential of -0.131 mPa (1.296 Atm., according to Christopher et. al Macromolecules 2003. 36:6888-6893). In this modified priming solution, the IR-GUS DNA was introduced and replicated as indicated by GUS expression as described in Examples 2 and 3 above.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. A method for introducing heterologous DNA into at least one cell of a plant seed embryo and priming the plant seed, comprising contacting an intact, dried plant seed which has not undergone imbibition with a priming medium containing a Geminivirus-based DNA construct comprising the heterologous DNA under conditions enabling priming and uptake of the DNA by said intact plant seed, said intact, dried plant seed comprising a seed coat, wherein the priming medium has a water potential enabling seed imbibitions but not radicle emergence thereby obtaining the seed embryo comprising the heterologous DNA and priming the plant seed.

2. The method of claim 1, further comprising the step of providing suitable conditions for subsequent seed germination and growth so as to obtain a plant or part thereof comprising the heterologous DNA.

3. The method of claim 1, wherein the DNA construct is a Begomovirus based construct.

4. The method of claim 1, wherein the Geminivirus is Tomato Yellow Leaf Curl Virus (TYLCV).

5. The method of claim 4, wherein said TYLCV based DNA construct comprises a polynucleotide sequence encoding:
  (i) a modification in a TYLCV coat protein (CP), wherein said modification comprises a deletion in nucleotides encoding an N-terminal 100 amino acids, wherein said modification results in a modified TYLCV V2 protein; and
  (ii) a modification in a TYLCV replicase, wherein said modification results in a reduced capability of rolling circle, single stranded DNA replication compared to an unmodified TYLCV replicase, and further when said modification of said TYLCV replicase results in a deletion in a C4 protein of said TYLCV, wherein said modifications are such that the construct is capable of systemic symptomless spread in a plant host.

6. The method of claim 1, wherein the DNA construct is an expression construct.

7. The method of claim 1, wherein the heterologous DNA encodes a protein.

8. The method of claim 1, wherein the heterologous DNA encodes a protein which confers a desirable agronomic trait selected from the group consisting of resistance to biotic or abiotic stress, increased yield, increased yield quality and preferred growth pattern.

9. The method of claim 1, wherein the heterologous DNA is transiently expressed in the at least one cell of the seed embryo and cells derived therefrom.

10. The method of claim 1, wherein the heterologous DNA is incorporated into the genome of the at least one cell of the seed embryo and cells derived therefrom.

11. The method of claim 1, wherein the seed is of a monocot origin.

12. The method of claim 1, wherein the seed is of a dicot origin.

13. The method of claim 1, wherein the seed is of cone-bearing origin.

14. The method of claim 1, wherein the introducing heterologous DNA into at least one cell of a plant seed embryo is not mediated by *Agrobacterium tumefaciens*.

15. The method of claim 4, wherein the DNA construct comprises a nucleic acid sequence which encodes the proteins. having an amino acid sequence as set forth in SEQ ID NOs: 3, the protein having an amino acid sequence as set forth in SEQ ID NO: 4 or the protein having an amino acid sequence as set fort in SEQ ID NO:-5.

16. The method of claim 5, wherein the DNA construct comprises the nucleic acid sequence set forth in SEQ ID NO:1 or SEQ ID NO:2.

* * * * *